United States Patent [19]
Young

[11] 3,975,236
[45] Aug. 17, 1976

[54] FERMENTATION PROCESSES FOR MAKING PENICILLIN AND CELLULASE

[75] Inventor: Murray Moo Young, Waterloo, Canada

[73] Assignee: The University of Waterloo, Waterloo, Canada

[22] Filed: Jan. 26, 1976

[21] Appl. No.: 652,301

[30] Foreign Application Priority Data
Aug. 11, 1975 Canada .............................. 233366

[52] U.S. Cl. ................................ 195/36 P; 195/65
[51] Int. Cl.² ..................... C12D 9/08; C12D 13/10
[58] Field of Search ................ 195/36 P, 65, 66 R, 195/114

[56] References Cited
OTHER PUBLICATIONS

Elmayergi et al., Journal of General Applied Microbiology, 1973, 19(5) 385–392.
Moo–Young, Chemical Abstracts, vol. 79, 1973, 144852h.

*Primary Examiner*—Lionel M. Shapiro
*Attorney, Agent, or Firm*—Sim & McBurney

[57] ABSTRACT

The presence of small dissolved quantities of carboxypolymethylenes in culture media producing cellulase or penicillin enhances the fermentation parameters.

7 Claims, No Drawings

FERMENTATION PROCESSES FOR MAKING PENICILLIN AND CELLULASE

FIELD OF INVENTION

This invention relates to the improvement of microbial fermentation processes by the incorporation of certain additives.

BACKGROUND TO THE INVENTION

In my pending U.S. application Ser. No. 497,306 filed Aug. 14, 1974, now U.S. Pat. No. 3,947,323 there is described the formation of amylase in an aqueous culture containing Aspergillus niger, a nutrient therefor and a small quantity of a polymeric material selected from a carboxypolymethylene, a polyacrylate and a polyethylene glycol. The presence of the polymeric material improves the microbial growth rate and the rate of product formation while the polymeric material is not consumed in the process.

SUMMARY OF INVENTION

It has now been surprisingly found that the presence of a small quantity of a carboxypolymethylene in an aqueous reaction medium producing cellulase from a Trichoderma species also enhances the fermentation parameters.

It has also been surprisingly found that the presence of a small quantity of a carboxypolymethylene in an aqueous medium producing penicillin from a Penicillium species and a nutrient therefor enhances the fermentation parameters.

GENERAL DESCRIPTION OF INVENTION

Microorganisms of the Trichoderma and Penicillium type are used in aerobic submerged fermentation processes.

To the culture in an aqueous nutrient medium of any convenient form, depending on the particular microorganism, is added the carboxypolymethylene, typically in a quantity from a trace to 1%.

The presence of this small quantity of polymer in the reaction medium results in enhancement of fermentation parameters, particularly microbial growth rate, the rate of product formation and the rate of substrate utilization.

The presence of the polymer in some way results in modification of the fermentation process resulting in increased mass transfer of nutrients and/or metabolites between the growing microorganism and fermentation medium.

The carboxypolymethylene is non-toxic to the microorganisms, apparently remains unconsumed in the culture, and is water-soluble. High molecular weight carboxypolymethylenes are preferred, such as that known as "Carbopol" 934.

In the one embodiment of the invention where cellulase is formed, the cellulose substrate may be in pure form or in an impure form, such as in cattle manure.

The Trichoderma species used preferably is Trichoderma viride and the culture also may contain other microorganisms, if desired, such as yeast strains, preferably Candida lipolytica or Sacchromyces cerevisiae.

In the second embodiment of the invention where penicillin is formed, the Penicillium species preferably is Penicillium notatum.

EXAMPLES

EXAMPLE I

Comparative tests were carried out using cultures of Trichoderma viride, ATCC 26921, to which 0.01% Carbopol 934 was added to the nutrient medium, whose pH is adjusted to 5 and containing:

| | |
|---|---|
| $KH_2PO_4$ | 3.0 g |
| $(NH_4)_2SO_4$ | 2.0 g |
| $CaCl_2$ | 0.3 g |
| Urea | 0.6 g |
| $MgSO_4.7H_2O$ | 0.3 g |
| $FeSO_4.7H_2O$ | 5.0 mg |
| $ZnSO_4.7H_2O$ | 1.4 mg |
| $MnSO_4.H_2O$ | 1.6 mg |
| $CoCl_2$ | 2.0 mg |
| Microcrystalline Cellulose | 5.0 g |
| Distilled Water | 1000 ml |

The system was innoculated by standard procedure using disrupted mycelia and incubated for a period of 5 days at 30°C.

The growth of the microorganism, the amount of cellulose degraded and the extracellular cellulase enzyme production as compared to that in a control medium to which no polymer was added, were measured at the end of the incubation period.

The results are reproduced in the following Table I:

TABLE I

| | |
|---|---|
| Relative growth rate: | 1.15 |
| Relative cellulose degradation: | 1.02 |
| Relative cellulase production: | 1.32 |

The results of this Table I show that enhancement effects of the polymer additive are obtained in the culture of Trichoderma viride.

EXAMPLE II

The procedure of Example I was repeated using a mixed culture of Trichoderma viride, ATCC 26921, and a special strain of the yeast, Candida lipolytica. The results are reproduced in the following Table II:

TABLE II

| | |
|---|---|
| Relative growth rate: | 1.56 |
| Relative cellulose degradation: | 1.09 |
| Relative cellulase production: | 2.52 |

The results of this Table II show that enhancement effects of the polymer additive are obtained in a mixed culture of Trichoderma viride and Candida lipolytica.

EXAMPLE III

Comparative tests were also carried out with cultures of Trichoderma viride using the medium of Example I in which the pure cellulose component was replaced with 25 g cattle manure with and without 0.01% Carbopol 934 additive with a pH adjusted to 4.5. The results of cellulose degradation of the manure are reproduced in the following Table III:

TABLE III

| Incubation Time (days) | Relative cellulose degradation |
|---|---|
| 4 | 1.42 |
| 8 | 1.33 |
| 12 | 1.20 |

TABLE III-continued

| Incubation Time (days) | Relative cellulose degradation |
|---|---|
| 16 | 1.16 |

The results of this Table III indicate that an enhancement effect of the polymer additive is also obtained with the degradation of cellulose substrate contained in cattle manure.

EXAMPLE IV

The procedure of Example III is repeated using a mixed culture of the *Trichoderma viride* and a yeast, *Sacchromyces cerevisiae*. The results of the cellulose degradation of the manure are shown in the following Table IV:

TABLE IV

| Incubation Time (days) | Relative Cellulose Degradation |
|---|---|
| 4 | 1.50 |
| 8 | 1.33 |
| 12 | 1.16 |
| 16 | 1.15 |

The results of the above Table IV show an enhancement effect of the polymer additive in a mixed culture of *Trichoderma viride* and *Sacchromyces cerevisiae*.

EXAMPLE V

Comparative tests were carried out using a culture of *Penicillium notatum*, with and without the addition of 0.3% Carbopol 934 and a nutrient medium of pH 5 containing:

| | |
|---|---|
| Glucose | 7.0 g |
| Lactice acid (neutralized to pH 7 with $NH_4OH$) | 3.5 g |
| $KH_2PO_4$ | 13.7 g |
| $KNO_3$ | 2.0 g |
| $MgSO_4$ | 1.2 g |
| $ZnSO_4 7H_2O$ | 0.002 g |
| $MnSO_4 H_2O$ | 0.010 g |
| $FeSO_4 7H_2O$ | 0.010 g |
| Distilled $H_2O$ | 1000 ml |

The relative amounts of carbon dioxide evolution, a measure of respiration activity, during the incubation period are reproduced in the following Table V:

TABLE V

| Incubation Period (days) | Relative $CO_2$ evolution |
|---|---|
| 2 | 3.0 |
| 4 | 3.2 |
| 6 | 3.4 |

The results of the above Table V show that the respiration activity is enhanced by the polymer additive.

SUMMARY

The present invention, therefore, provides enhancement of the fermentation parameters of particular fermentation processes by the incorporation in the culture of a certain polymer. Modifications are possible within the scope of the invention.

What I claim is:

1. A fermentation process, which comprises forming cellulase in an aqueous medium containing a Trichoderma species, cellulose and a small quantity of a carboxypolymethylene.

2. The process of claim 1 wherein said Trichoderma species is *Trichoderma viride*.

3. The process of claim 1 wherein said Trichoderma species is *Trichoderma viride* and said aqueous medium also contains *Candida lipolytica*.

4. The process of claim 1 wherein said Trichoderma species is *Trichoderma viride* and said aqueous medium also contains *Sacchromyces cerevisiae*.

5. The process of claim 1 wherein said cellulose is provided by cattle manure.

6. A fermentation process, which comprises forming penicillin in an aqueous medium containing a Penicillium species, a nutrient therefor and a small quantity of a carboxypolymethylene.

7. The process of claim 6 wherein said Penicillium species is *Penicillium notatum*.

* * * * *